US009545149B1

(12) United States Patent
Vila et al.

(10) Patent No.: US 9,545,149 B1
(45) Date of Patent: Jan. 17, 2017

(54) HYGIENIC TOOTHBRUSH MAINTENANCE SYSTEM

(71) Applicants: Luis Vila, Miami, FL (US); Mariela Alvarado, Miami, FL (US)

(72) Inventors: Luis Vila, Miami, FL (US); Mariela Alvarado, Miami, FL (US)

( * ) Notice: Subject to any disclaimer, the term of this patent is extended or adjusted under 35 U.S.C. 154(b) by 0 days.

(21) Appl. No.: 14/944,389

(22) Filed: Nov. 18, 2015

(51) Int. Cl.

| | |
|---|---|
| ***A61N 5/06*** | (2006.01) |
| ***A46B 17/06*** | (2006.01) |
| ***A46B 5/00*** | (2006.01) |
| ***A46B 17/04*** | (2006.01) |
| ***A46B 15/00*** | (2006.01) |
| ***B08B 7/00*** | (2006.01) |

(52) U.S. Cl.
CPC ........... *A46B 17/065* (2013.01); *A46B 5/0095* (2013.01); *A46B 15/0095* (2013.01); *A46B 17/04* (2013.01); *B08B 7/0057* (2013.01); *A46B 2200/1066* (2013.01); *B08B 2240/00* (2013.01)

(58) Field of Classification Search
CPC ..... A46B 17/065; A46B 5/0095; A46B 17/04; A46B 15/0095; A46B 2200/1066; B08B 7/0057; B08B 2240/00
USPC ........................................ 250/455.11, 504 R
See application file for complete search history.

(56) References Cited

U.S. PATENT DOCUMENTS

2009/0056044 A1* 3/2009 Rizoiu .................. A46B 5/002 15/22.1
2014/0166900 A1* 6/2014 Nelson ...................... A61L 2/10 250/455.11

* cited by examiner

*Primary Examiner* — Michael Maskell
(74) *Attorney, Agent, or Firm* — Ruben Alcoba, Esq

(57) ABSTRACT

A hygienic toothbrush maintenance system helps maintain a toothbrush in a hygienic state through use of at least one detachable head that can be interchanged, and ultraviolet light that immerses bristles to kill bacteria. A pair of tensioned wires on the detachable head slides in and out of a head end of the toothbrush to enable secure and easy detachable attachment of the detachable head from the toothbrush. A release switch enables detachment of the detachable head from the toothbrush, and is operable with one hand so as to minimize contact with the toothbrush. A docking platform retains the toothbrush in an upright position and stores the removed detachable heads. An ultraviolet portion includes a telescopically extendable stand and a hood that emits ultraviolet light. The hood pivots to substantially cover the detachable heads, while they are attached to the toothbrush, and while stored in a head reception portion.

20 Claims, 6 Drawing Sheets

HYGIENIC TOOTHBRUSH MAINTENANCE SYSTEM

BACKGROUND

Figure 1A:
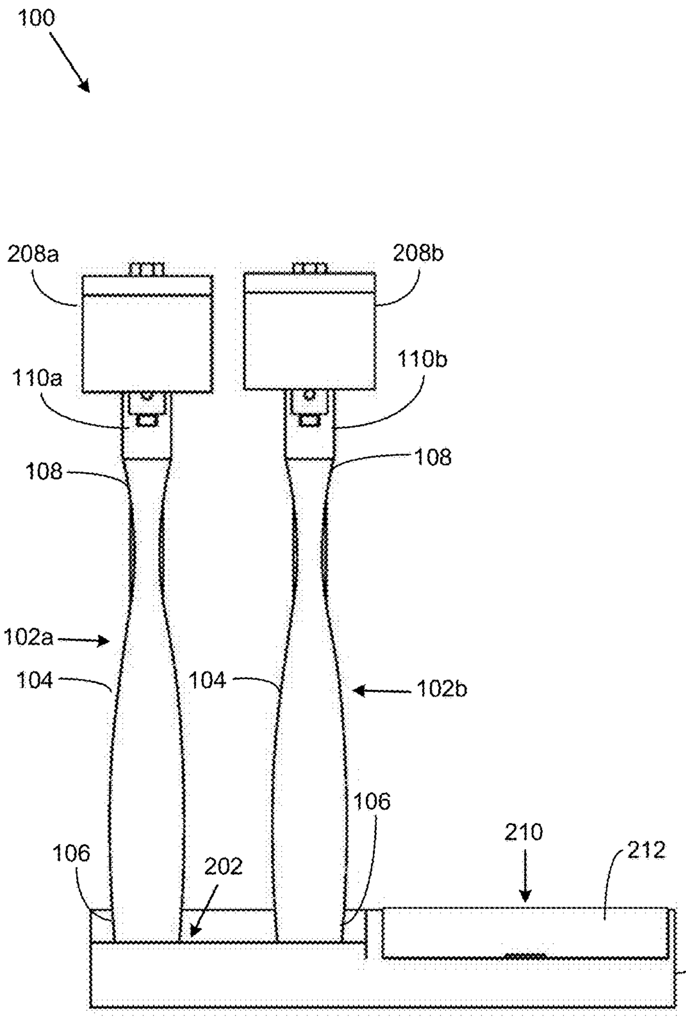

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The present invention is directed to a hygienic toothbrush maintenance system that utilizes a detachable head, a controllable ultraviolet light, a protective cartridge, and a one-handed release switch to maintain hygienic conditions for a toothbrush.

A toothbrush is an oral hygiene instrument used to clean the teeth and gums that consists of a head of tightly clustered bristles mounted on a handle, which facilitates the cleansing of hard-to-reach areas of the mouth. The bristles of the toothbrush are often covered with toothpaste to increase the effectiveness of tooth brushing.

It is known in the art that the value of a continuous and thorough dental hygiene program with a toothbrush is effective for the prevention of dental caries, periodontal diseases and deterioration of tooth surfaces caused by bacterial infection in the mouth.

The inventor knew that cavities are developed in teeth as a result of chemical reaction with the tooth surface caused by bacteria constantly present in the mouth. The bacteria produce acids and similar toxins which attack the surface of the teeth and dissolve the surfaces thus producing cavities which must be repaired in order to save the tooth. The inventor was also aware that, since tooth decay and peridental diseases may be affected by bacterial action, there was a need for destroying these bacteria colonies which form on tooth surfaces.

Through years of brushing and dentist visits, the inventor also knew that the primary function of a toothbrush is to destroy colonies of bacteria and remove plaque so that there will be no buildup in the concentration of plaque and bacteria which will attack the various structures of the mouth.

However, the inventor recognized that a toothbrush is also a source of bacterial contamination. Microscopic particles or larger particles frequently become lodged in the bristles and then they reenter the mouth on the next brush of the teeth.

Further, the inventor noticed that toothbrush users often discarded toothbrushes every few months, or even weeks. Through research, the inventor learned that it takes less than three weeks for bacteria to heavily infect the bristles of brushes constantly used in warm environments.

The inventor also recognized a societal trend in that society was moving away from the disposable era toward an era of conservation of resources. Thus, throwing away a toothbrush every two weeks was no longer acceptable. The inventor recognized that not only do such habits waste the natural resources used in producing the toothbrush, but toothbrushes are commonly made of materials which do not easily degrade in landfills, which contributes to the general problem of using up available disposal sites.

The inventor wondered if the most bacteria susceptible portion of the tooth brush could be removed for cleaning or interchanging. The inventor developed a toothbrush with a disposable bristle head, which would allow the user to dispose only a part of the brush, rather than the whole brush. The inventor saw that this created a more acceptable environmentally and encourages frequent discarding of the contaminated bristles; thus minimizing the potential of reinfection of the mouth with bacteria.

In addition, the inventor saw that the toothbrush with a detachable head could allow other dental appliances such as picks or bristle heads with differently shaped or different stiffness bristles to be mounted on the handle.

However, the inventor recognized a problem in that the bristles were still not being cleaned thoroughly. The inventor researched and learned that ultraviolet light was effective for killing 99.9% of bacteria. The inventor developed a stand and a hood with reflective interior. An ultraviolet light source was positioned in the hood to immerse the detachable head. The inventor also made the head pivotable so as to optimize engagement with the detachable head.

Dental hygienic systems have been utilized in the past; yet none with the characteristics of the present invention. See U.S. Pat. Nos. 9,095,634; 6,786,342; and 20060085932.

For the foregoing reasons, there is a hygienic toothbrush maintenance system that maintains the hygiene of a toothbrush, and specifically the bristles of the toothbrush through use of a detachable head, a controllable ultraviolet light portion, a protective cartridge, and a one-handed release switch to maintain hygienic conditions for a toothbrush.

SUMMARY

The present invention describes a hygienic toothbrush maintenance system. The hygienic toothbrush maintenance system, hereafter, "system" utilizes a detachable head, a controllable ultraviolet light portion, a protective cartridge, and a one-handed release switch to maintain hygienic conditions for a toothbrush.

In one embodiment, the system helps maintain a toothbrush in a hygienic state through use of at least one detachable head that can be interchanged, and ultraviolet light that substantially immerses the bristles to kill bacteria. A pair of tensioned wires on the detachable head slides in and out of a head end of the toothbrush to enable secure and easy detachable attachment of the detachable head from the toothbrush. A release switch enables detachment of the detachable head from the toothbrush, and is operable with one hand so as to minimize contact with the toothbrush. A docking platform retains the toothbrush in an upright position and stores the removed detachable heads. An ultraviolet portion includes a telescopically extendable stand and a hood that emits ultraviolet light. The hood pivotally covers the detachable heads, while they are attached to the toothbrush, and while stored in a head reception portion.

In some embodiments, the system may include a toothbrush. The toothbrush comprises at least one detachable head having a plurality of bristles. The detachable head may be U-shaped to fit into the head end of the toothbrush. In one embodiment, a fastening mechanism, such as a pair of tensioned wires, may be used to detach and attach the detachable head to the head end of the toothbrush.

In one embodiment, the pair of tensioned wires may extend from the head end of the toothbrush and engage a pair of depressions in the detachable head to lock the detachable head to the head end of the toothbrush. A release switch on the head end of the toothbrush is operatively connected to the tensioned wires, and may be manipulated to release tension from the tensioned wires. The release switch may be operated with one hand, so as to minimize contact with the hands, and thereby further enhance the hygienic qualities of the system.

The detachable head may also have a back side with a textured surface for scrubbing the gums, and a front side from which the bristles extend. The detachable head may be interchanged onto the head end of the toothbrush with other detachable heads having various sizes, colors, and shapes. In one embodiment, at least one cartridge detachably encases the detachable head to provide protection against external elements.

A docking platform provides a foundation for supporting the toothbrush in an upright position, and for storing the at least one detachable head when not in use. The docking platform includes at least one toothbrush reception portion that detachably receives to the handle end of the toothbrush. By orienting the toothbrush in the upright position in the toothbrush reception portion, excess water may flow away from the bristles; thereby minimizing bacterial growth. The docking platform further comprises at least one head reception portion that is shaped and sized to receive the at least one detachable head while encased in the cartridge. In this manner, the detachable heads can be selected based on desired hygienic readiness, hardness of bristles, or decorative aspects.

In some embodiments, the system utilizes ultraviolet light to kill bacteria that accumulates on the detachable head, and specifically bacteria on the bristles. At least one ultraviolet portion is disposed on the docking platform, adjacent to the toothbrush, and oriented to emit ultraviolet light directly on the bristles of the detachable head.

In one embodiment, the ultraviolet portion may include a stand and a hood. The stand provides a supportive component for the hood. In one embodiment, each stand rests parallel and adjacent to each toothbrush on the platform. The stand may be configured to telescopically extend and retract.

The stand extends from a base section of the ultraviolet portion, terminating at the hood. The hood is configured to position over and partially encapsulate the detachable head. The hood may be swiveled, pivoted, and detached to enable access to the detachable head that is attached to the head end of the toothbrush. The stand may be lowered, such that the light source immerse the unused detachable heads in their respective head reception portion.

The hood includes an interior reflective surface having reflective qualities. The interior reflective surface further includes a light source that emits ultraviolet light. The ultraviolet light emitted by the light source reflects off the interior surface to fully immerse the bristles of the toothbrush.

A hygienic toothbrush maintenance system, the system comprising:

at least one toothbrush, the at least one toothbrush comprising a longitudinal axis, a head end, and a handle end;

at least one detachable head, the at least one detachable head comprising a front side having a plurality of bristles and a back side having a pair of depressions;

a cartridge, the cartridge configured to detachably encase the at least one detachable head;

a pair of tensioned wires, the pair of tensioned wires configured to exert a tension force, the pair of tensioned wires further configured to extend from the head end of the at least one toothbrush, the pair of tensioned wires further configured to engage the pair of depression in the back side of the at least one detachable head, whereby the pair of tensioned wires generate sufficient tension to at least partially fasten the at least one detachable head to the head end of the at least one toothbrush; a release switch, the release switch configured to operatively connect to the pair of tensioned wires, the release switch further configured to at least partially release tension from the pair of tensioned wires, whereby releasing the tension enables the pair of tensioned wires in the head end of the at least one toothbrush to disengage from the pair of depressions of the at least one detachable head;

a docking platform, the docking platform comprising at least one toothbrush reception portion, the at least one toothbrush reception portion configured to receive the handle end of the toothbrush, the docking platform further comprising at least one head reception portion, the at least one head reception portion configured to receive the at least one disposable head; and an ultraviolet portion, the ultraviolet portion comprising a stand, a hood, and a light source, the stand disposed adjacent to the at least one toothbrush, the hood configured to selectively cover the at least one detachable head, the hood comprising an interior reflective surface, the light source configured to emit an ultraviolet light, whereby the ultraviolet light reflects off the interior reflective surface for substantially immersing the at least one detachable head with ultraviolet light.

In another aspect, the at least one toothbrush is a manual toothbrush.

In another aspect, the at least one toothbrush is three toothbrushes.

In another aspect, the plurality of bristles in the at least one detachable head are fabricated from an antibacterial synthetic polymer.

In another aspect, the at least one detachable head is six detachable heads.

In yet another aspect, back side of the at least one detachable head is textured.

In yet another aspect, the cartridge is transparent.

In yet another aspect, the pair of tensioned wires are parallel.

In yet another aspect, the pair of tensioned wires terminate at a hook.

In yet another aspect, the hook is configured to engage the pair of depressions.

In yet another aspect, the release switch is disposed at the head end of the toothbrush.

In yet another aspect, the release switch is configured to be operable with one hand.

In yet another aspect, a pair of lateral edges of the at least one disposable head slidably engage the pair of tensioned wires.

In yet another aspect, docking platform is substantially rectangular.

In yet another aspect, the docking platform is fabricated from an antibacterial polymer.

In yet another aspect, the hood selectively covers the at least one detachable head during attachment to the head end of the at least one toothbrush, or during storage in the at least one head reception portion of the docking platform.

In yet another aspect, the hood is configured to pivot.

In yet another aspect, the hood is dome-shaped.

In yet another aspect, the stand is configured to telescopically extend and retract.

In yet another aspect, the light source is an excimer lamp.

One objective of the present invention is to provide a hygienic environment for a toothbrush.

Another objective of the present invention is to provide at least one detachable head that operates on a toothbrush and enables selective changing of heads and bristles for hygiene, bristle strength, and style.

Another objective of the present invention is to provide more detachable heads than toothbrushes.

Yet another objective of the present invention is to provide a protective cartridge for the detachable head, and especially the bristles.

Yet another objective is to provide a toothbrush reception portion that snugly receives the handle end of the toothbrush.

Yet another objective is to kill bacteria on the bristles with ultraviolet light.

Yet another objective is to minimize contact with the toothbrush by providing a release switch that is operable with one hand.

Yet another objective is to provide an inexpensive to manufacture toothbrush with hygienic features.

DRAWINGS

Figure 1B:
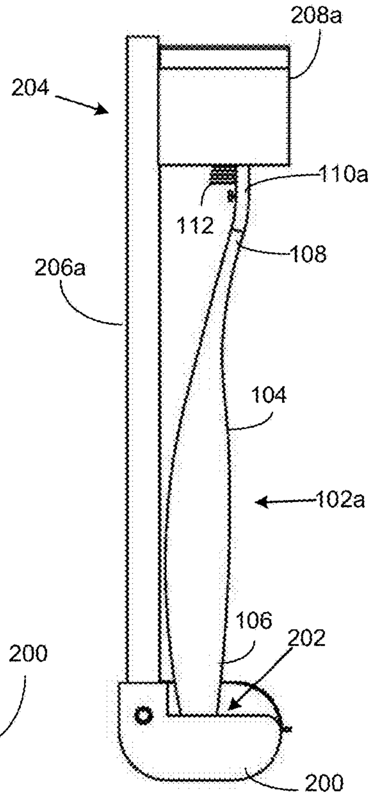
Figure 2A:
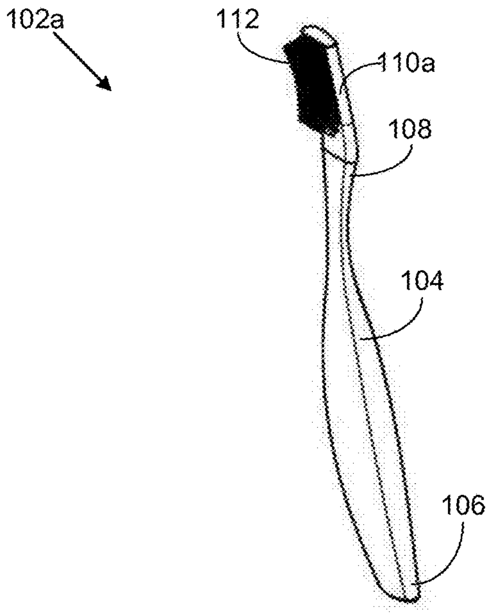
Figure 2B:
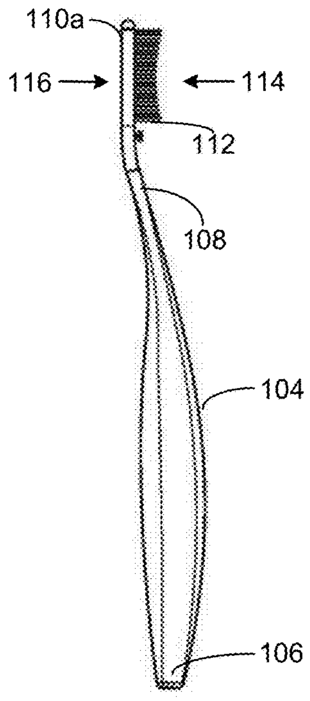
Figure 2C:
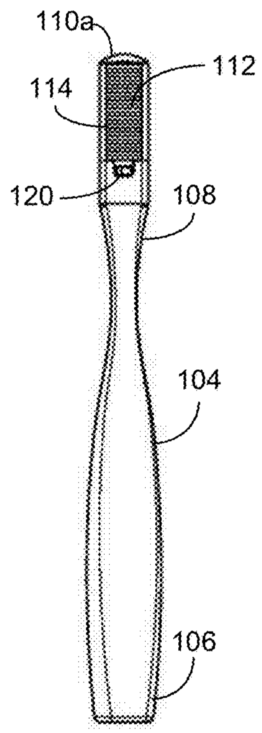
Figure 2D:
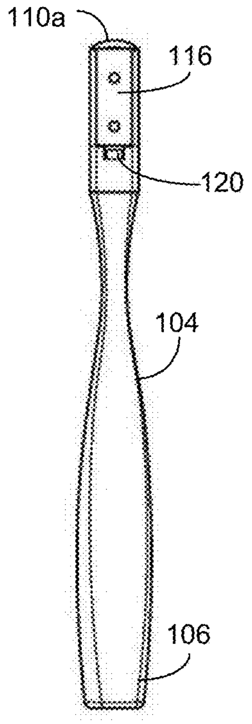
Figure 3A:
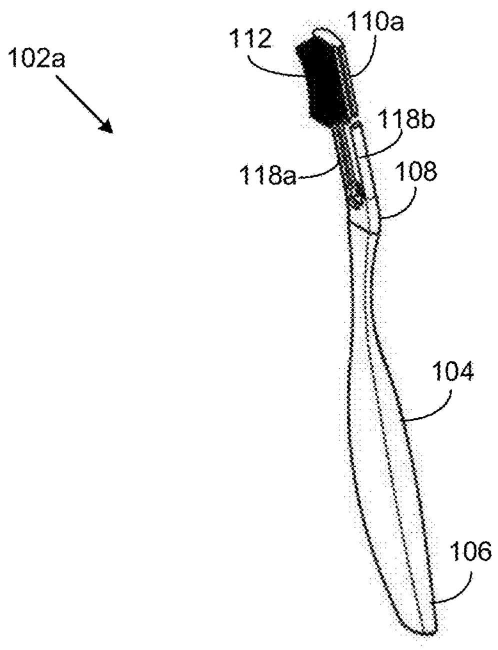
Figure 3B:
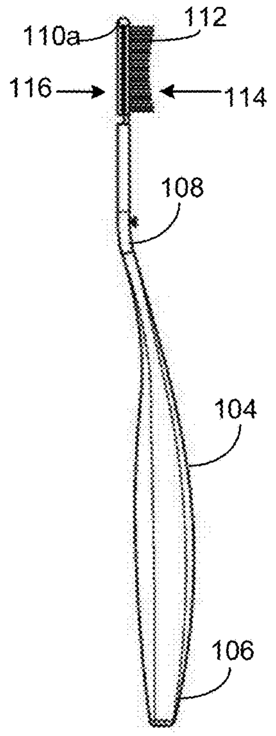
Figure 3C:
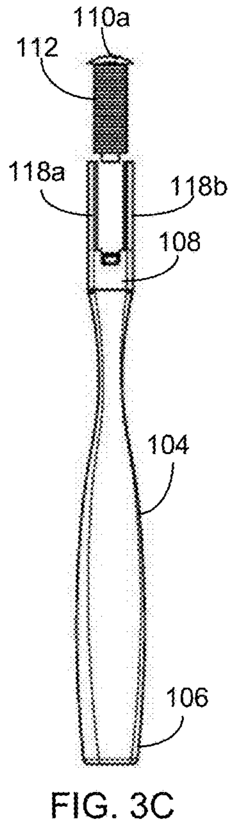
Figure 3D:
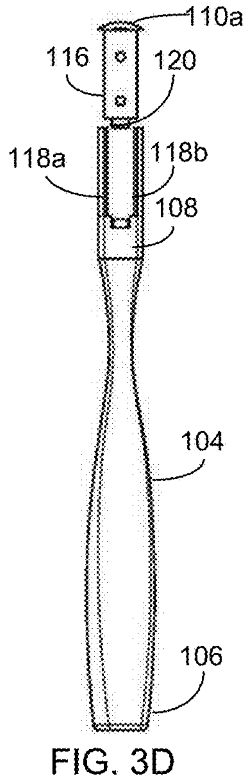
Figure 4:
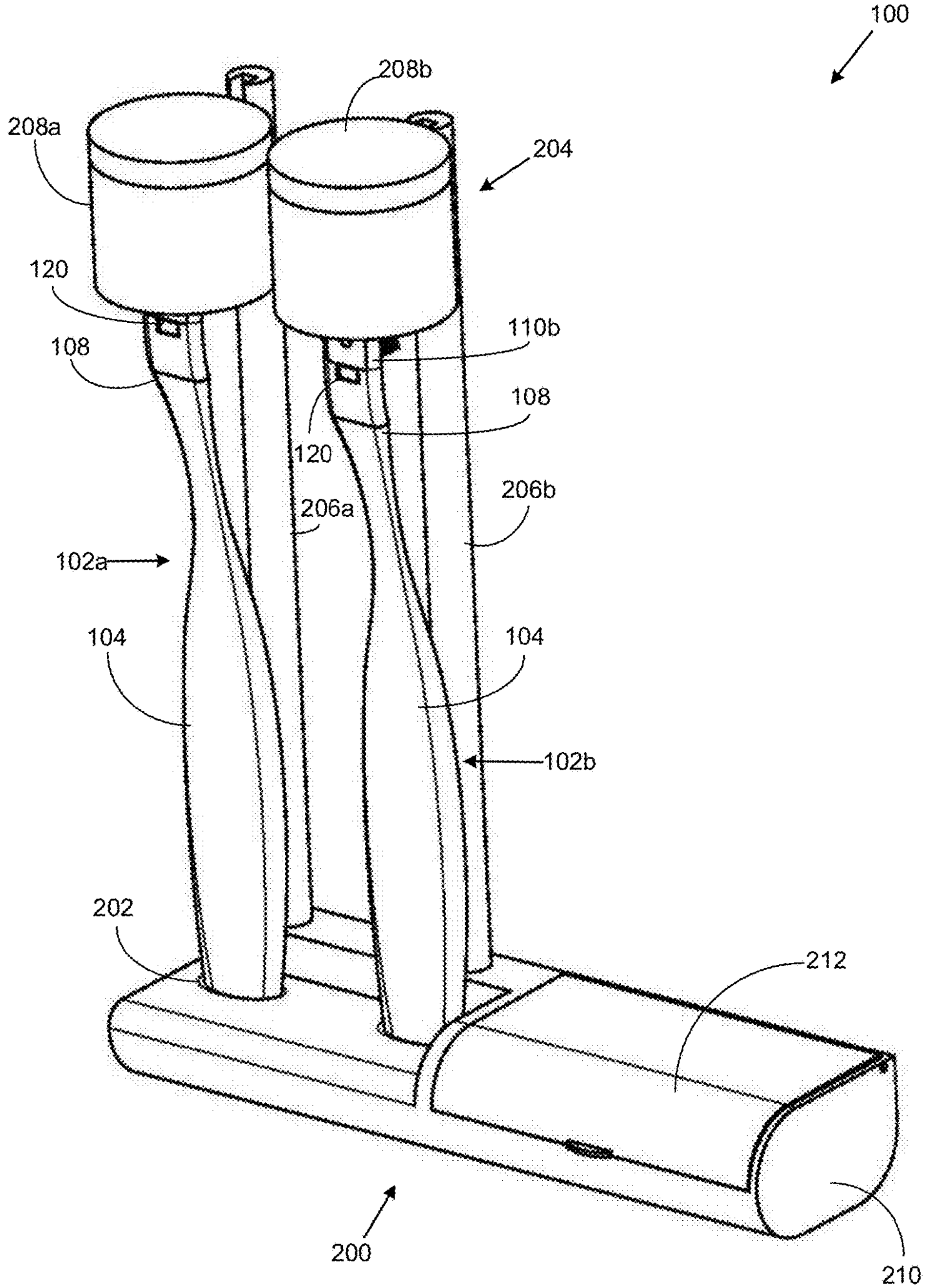
Figure 5:
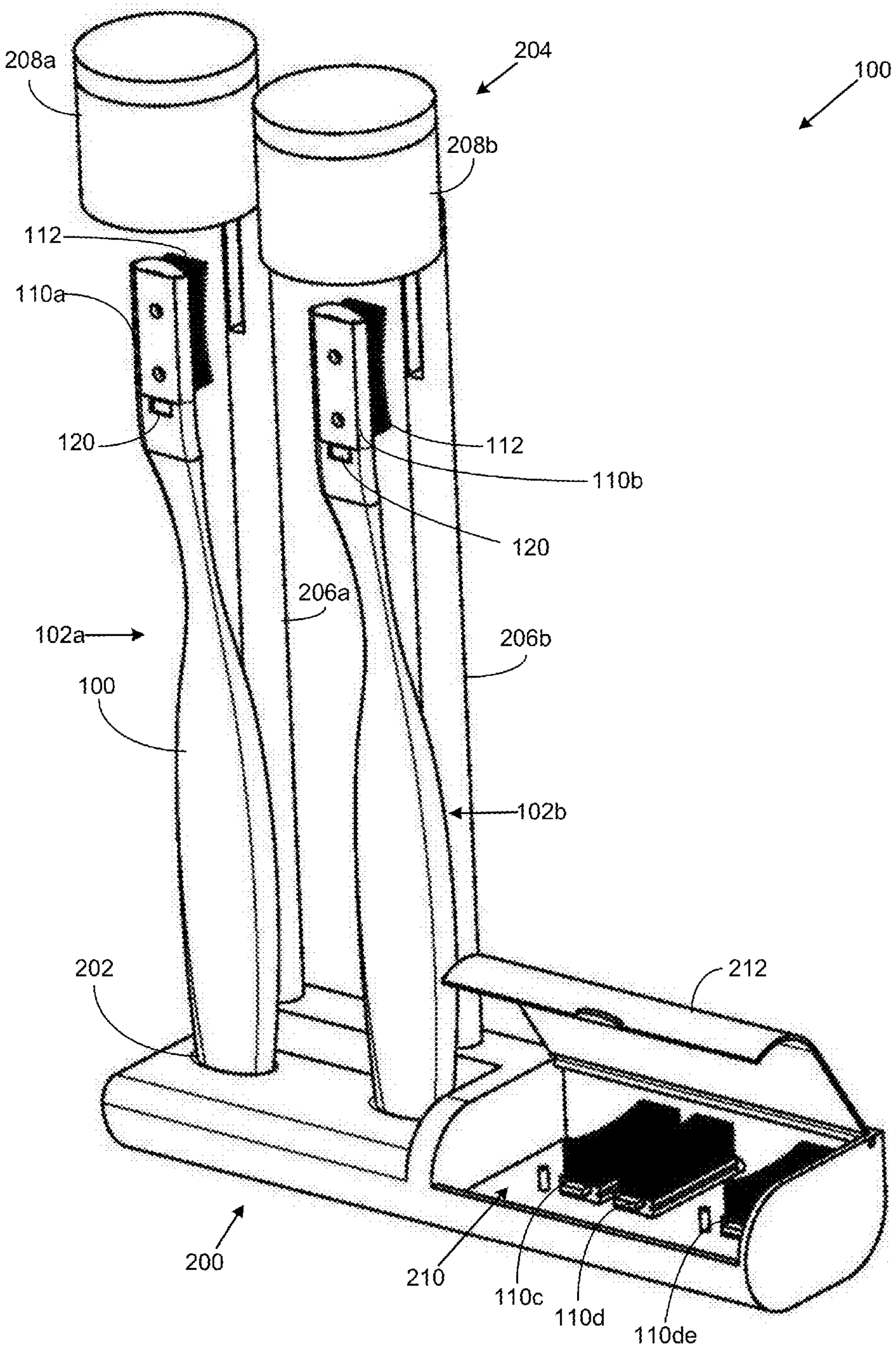
Figure 6:
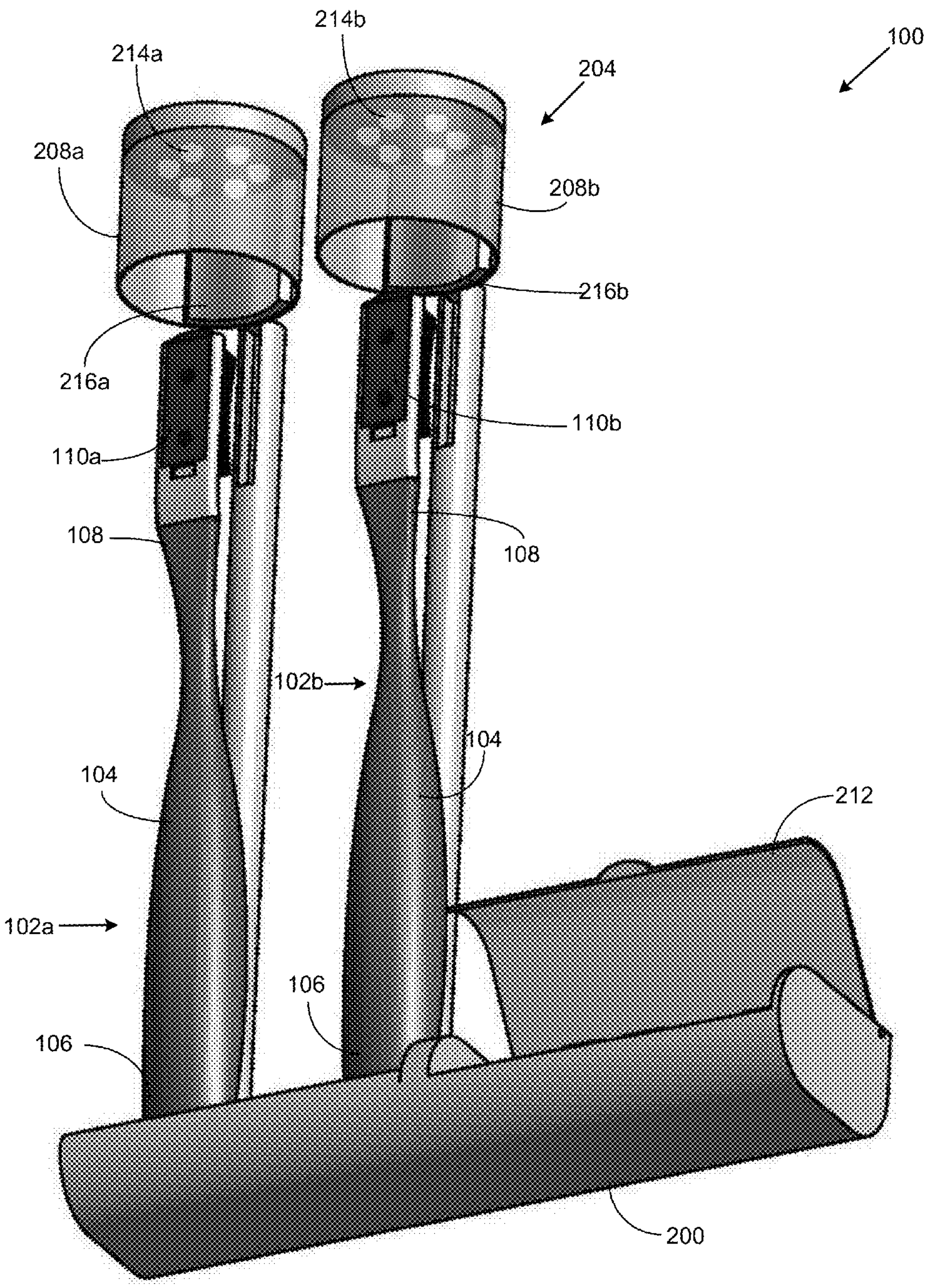

These and other features, aspects, and advantages of the present invention will become better understood with regard to the following description, appended claims, and drawings where:

FIGS. 1A and 1B are views of an exemplary hygienic toothbrush maintenance system, where FIG. 1A is a perspective view, and FIG. 1B is an elevated side view;

FIGS. 2A, 2B, 2C, and 2D are views of an exemplary toothbrush with an exemplary detachable head attached, where FIG. 2A is a perspective view, and FIG. 2B is an elevated side view, FIG. 2C is a frontal view, and FIG. 2D is a back view;

FIGS. 3A, 3B, 3C, and 3D are views of a toothbrush with a detachable head detached, where FIG. 3A is a perspective view, and FIG. 3B is an elevated side view, FIG. 3C is a frontal view, and FIG. 3D is a back view;

FIG. 4 is a perspective view of a hygienic toothbrush maintenance system showing an exemplary hood covering a detachable head, and a lid in a closed position over a head reception portion of a docking platform;

FIG. 5 is a perspective view of a hygienic toothbrush maintenance system showing a hood removed from a detachable head, and a lid in an open position over a head reception portion of a docking platform; and FIG. 6 is a lower angle perspective view of a hygienic toothbrush maintenance system showing an exemplary ultraviolet light source and an exemplary reflective surface of an exemplary ultraviolet portion.

DESCRIPTION

The present invention, a referenced in FIGS. 1A-6, is directed to a hygienic toothbrush maintenance system 100, hereafter, "system 100" that helps maintain a toothbrush 102*a-b* in a hygienic state through use of at least one detachable head 110*a-e*, a controllable ultraviolet light portion 204, a protective cartridge (not shown), and a one-handed release switch 120. The hygienic toothbrush 102*a-b* maintenance system 100 helps maintain a toothbrush 102*a-b*, and especially the bristles 112 of the toothbrush 102*a-b* that engage the teeth, in a hygienic state through multiple hygiene-based components and instruments that together create a synergy for optimal hygiene of the toothbrush 102*a-b*; and thereby the mouth in which the toothbrush 102*a-b* operates.

As referenced in FIG. 1A, the system 100 may include at least one detachable head 110*a-e* that can be interchanged with one hand, and a controllable ultraviolet light portion 204 that pivots, extends, and retracts to substantially immerse the detachable head 110*a-e*, including a plurality of bristles 112, in ultraviolet light for efficient killing of bacteria.

In another embodiment, a pair of tensioned wires 118*a-b* on the detachable head 110*a-e* slides in and out of a head end 108 of the toothbrush 102*a-b* to enable secure and easy detachable attachment of the detachable head 110*a-e* from the toothbrush 102*a-b*. A release switch 120 enables detachment of the detachable head 110*a-e* from the toothbrush 102*a-b*. The release switch 120 is operable with one hand so as to minimize contact with the toothbrush 102*a-b*.

Looking now at FIG. 1B, a docking platform 200 retains the toothbrush 102*a-b* in an upright position and stores the removed detachable heads 110*a-e*. An ultraviolet portion 204 includes a telescopically extendable stand 206*a-b* that positions a hood 208*a-b* over the detachable head 110*a-e*. The hood includes an interior reflective surface 216*a-b* and an ultraviolet light source 214*a-b* that emits ultraviolet light. The hood 208*a-b* pivotally covers the detachable head 110*a-e*, while attached to the toothbrush 102*a-b*, or while stored in a head reception portion 210.

As illustrated in FIG. 2A, the system 100 is operable with at least one toothbrush 102*a* defined by a handle end 106, a head end 108, a longitudinal axis 104. In one embodiment, the at least one toothbrush 102*a-b* is a manual toothbrush with an elongated longitudinal axis 104 fabricated from a rigid polymer. As shown in FIGS. 2B and 2C, the system 100 specifically addresses at least one detachable head 110*a-e* having a plurality of bristles 112 that detachably attach to the head end 108 of the toothbrush 102*a-b*. The system 100 enables one-handed removal of the detachable head 110*a-e* for cleaning and maintenance, and also immerses the detachable head 110*a-e* with ultraviolet light to kill bacteria on the bristles 112 of the detachable head 110*a*.

Those skilled in the art will recognize that the bristles 112 are the portion of the toothbrush 102*a-b* that are most susceptible to bacteria, as they are the portion of the toothbrush 102*a-b* that most intimately engage the teeth in the deepest recesses of the mouth. For example, microscopic particles or larger particles frequently become lodged in the bristles 112 and then reenter the mouth on subsequent brushing of the teeth. Thus, as FIG. 2D shows, to ensure the bristles 112 are not overused, the toothbrush 102*a-b* comprises at least one detachable head 110*a-e* having a plurality of bristles 112.

Looking now at FIG. 3A, the detachable head 110*a-e* may be U-shaped to fit into the head end 108 of the toothbrush 102*a-b*. As FIGS. 2B and 3B reference, the detachable head 110*a-e* includes a front side 114 from which the bristles 112 extend. The bristles 112 are configured to intimately engage the teeth. Suitable materials for the bristles 112 may include a synthetic polymer, such as nylon. The detachable head 110*a-e* further comprises a back side 116, which may have a textured surface. The textured surface may be used to clean the gums and tongue. It is also significant to note that enabling detachment of the bristles 112 allows a user to change colors or bristle hardness; for example, hard, middle, and soft bristles 112.

Turning now to FIG. 3C, a fastening mechanism, such as a pair of tensioned wires 118*a-b*, may be used to detach and attach the detachable head 110*a-e* to the head end 108 of the toothbrush 102*a-b*. In one possible embodiment, the pair of tensioned wires 118*a-b* include two parallel wires 118*a-b* or flexible rods that terminate at a hook. The hook is configured to engage the pair of depressions in the detachable head 110*a-e*.

As shown in FIG. 3D, the pair of tensioned wires 118*a-b* may extend from the head end 108 of the toothbrush 102*a-b* and engage a pair of depressions in the detachable head 110*a-e* to lock the detachable head 110*a-e* to the head end 108 of the toothbrush 102*a-b*. Though in alternative embodiments, various other fastening mechanisms may be used, including magnets, friction fit connectors, and threaded male and female connectors.

As FIGS. 2C and 3C illustrate, a release switch 120 positions on the head end 108 of the toothbrush 102*a-b*. The release switch 120 is operatively connected to the tensioned wires 118*a-b*. The release switch 120 may be manipulated to release tension from the tensioned wires 118*a-b*. In one embodiment, the release switch 120 moves along the length of the longitudinal axis 104 of the toothbrush 102*a-b*. The release switch 120 is biased to a lock position. Applying a longitudinal force to the release switch 120 pries open the hooks of the tensioned wires 118*a-b* to release from the depressions in the detachable head 110*a-e*. The release switch 120 may be operated with one hand, so as to minimize contact with the hands, and thereby further enhance the hygienic qualities of the system 100.

In one alternative embodiment, the head end 108 of the toothbrush 102*a-b* allows other dental appliances such as picks or bristle heads with differently shaped or different stiffness bristles 112 to be mounted on the toothbrush 102*a-b*. In these cases, the dental appliances couple with the pair of tensioned wires 118*a-b*, substantially the same as the detachable head 110*a-e*.

The detachable head 110*a-e* may also have a back side 116 with a textured surface for scrubbing the gums, and a front side 114 from which the bristles 112 extend. The detachable head 110*a-e* may be interchanged onto the head end 108 of the toothbrush 102*a-b* with other detachable head 110*a-es* having various sizes, colors, and shapes. In one embodiment, at least one cartridge detachably encases the detachable head 110*a-e* to provide protection against external elements.

In one embodiment, a cartridge is configured to encase the detachable head 110*a-e* when not in use. This provides an additional layer of hygiene. The cartridge may include a transparent case that is sized and dimensioned to at least partially encapsulate the detachable head 110*a-e*. The cartridge may be used on the detachable head 110*a-e* while attached to the toothbrush 102*a-b*, or while detached. Suitable materials for the cartridge may include, without limitation, a transparent plastic, a rigid polymer, a polyurethane, stainless steel and fiberglass.

Looking next at FIG. 4, a docking platform 200 provides a foundation for supporting the toothbrush 102*a-b* in an upright position, and for storing the at least one detachable head 110*a-e* when not in use. In one embodiment, the docking platform 200 is rectangular shaped, and fabricated from an antibacterial material.

In some embodiments, the docking platform 200 includes at least one toothbrush 102*a-b* reception portion that detachably receives to the handle end 106 of the toothbrush 102*a-b*. The toothbrush 102*a-b* reception portion may include a slot that is sized and dimensioned to snugly receive the handle end 106 of the toothbrush 102*a-b*. By orienting the toothbrush 102*a-b* in the upright position in the toothbrush 102*a-b* reception portion, excess water may flow away from the bristles 112; thereby minimizing bacterial growth.

As FIG. 5 references, the docking platform 200 further comprises at least one head reception portion 210. The head reception portion 210 is shaped and sized to receive the at least one detachable head 110*a-e* while encased in the cartridge, or while not encased in the cartridge. A lid 212 may hingedly cover the head reception portion 210. In this manner, multiple detachable head 110*a-es* can be selected based from their appropriate head reception portion 210 based on desired hygienic readiness, hardness of bristles 112, or decorative aspects. For example, the detachable head 110*a-es* may include a red color having hard bristles; a blue color having soft bristles; and a yellow with sparkles color having medium bristles. The docking platform 200 may be fabricated from an antibacterial polymer or stainless steel.

In some embodiments, the system 100 utilizes ultraviolet light to kill bacteria that accumulates on the detachable head 110*a-e*, and specifically bacteria on the bristles 112. The ultraviolet light is controllable so as to optimize engagement with the detachable head 110*a-e*, and specifically the bristles 112 of the toothbrush 102*a-b*. At least one ultraviolet portion 204 is disposed on the docking platform 200, adjacent to the toothbrush 102*a-b*, and oriented to emit ultraviolet light directly on the bristles 112 of the detachable head 110*a-e*.

As referenced in FIG. 6, the ultraviolet portion 204 may include a stand 206*a-b* and a hood 208*a-b*. The stand 206*a-b* provides a supportive component for the hood 208*a-b*. In one embodiment, each stand 206*a-b* rests parallel and adjacent to each toothbrush 102*a-b* on the platform 200. The stand 206*a-b* may be configured to telescopically extend and retract, so as to enable selective covering and uncovering from the at least one detachable head 110*a-e*.

The stand 206*a-b* extends from a base section of the docking platform 200, terminating at the hood 208*a-b*. The hood 208*a-b* is configured to position over and partially encapsulate the detachable head 110*a-e*. The hood 208*a-b* may be swiveled, pivoted, and detached to enable access to the detachable head 110*a-e* while it is attached to the head end 108 of the toothbrush 102*a-b*, or stored in the head reception portion 210 of the docking platform 200. For example, the stand 206*a-b* may be lowered, such that the ultraviolet light source 214*a-b* immerse the unused detachable heads 110*a-e* in their respective head reception portion 210. In one embodiment, the stand 206*a-b* telescopically extends and retracts, so as to enable controllable interaction with the detachable head 110*a-e*.

The hood 208*a-b* includes an interior reflective surface 216*a-b* having reflective qualities (FIG. 6). The hood 208*a-b* may be dome-shaped, or any shape and size that is sufficient to at least partially cover the detachable head 110*a-e*. The hood 208*a-b* may be fabricated from metal, stainless steel, or any reflective material or material coated with a reflective composition. The interior reflective surface 216*a-b* of the hood 208*a-b* further includes a light source 214*a-b* that emits ultraviolet light.

In one embodiment, the ultraviolet light source 214*a-b* is an excimer lamp. The ultraviolet light emitted by the light source 214*a-b* reflects off the interior surface to fully immerse the bristles 112 of the toothbrush 102*a-b*. Those skilled in the art, in light of the present teachings, will recognize that ultraviolet light is an electromagnetic radiation with a wavelength from 400 nm to 100 nm, shorter than that of visible light but longer than X-rays. This range of wavelengths is efficacious for killing bacteria.

In some embodiments, the stand 206*a-b* may be manipulated to obtain optimal immersion of the detachable head

110*a-e* in the ultraviolet light. Thus, the hood 208*a-b* selectively covers the at least one detachable head 110*a-e* during attachment to the head end 108 of the toothbrush 102*a-b*, or when the detachable head 110*a-e* is detached from the toothbrush 102*a-b*, during storage in the at least one head reception portion 210 of the docking platform 200.

While the inventor's above description contains many specificities, these should not be construed as limitations on the scope, but rather as an exemplification of several preferred embodiments thereof. Many other variations are possible. For example, the system may store dental floss in the docking platform. Accordingly, the scope should be determined not by the embodiments illustrated, but by the appended claims and their legal equivalents.

What is claimed is:

1. A hygienic toothbrush maintenance system, the system comprising:

at least one toothbrush, the at least one toothbrush comprising a longitudinal axis, a head end, and a handle end;

at least one detachable head, the at least one detachable head comprising a front side having a plurality of bristles and a back side having a pair of depressions;

a cartridge, the cartridge configured to detachably encase the at least one detachable head;

a pair of tensioned wires, the pair of tensioned wires configured to exert a tension force, the pair of tensioned wires further configured to extend from the head end of the at least one toothbrush, the pair of tensioned wires further configured to engage the pair of depression in the back side of the at least one detachable head, whereby the pair of tensioned wires generate sufficient tension to at least partially fasten the at least one detachable head to the head end of the at least one toothbrush;

a release switch, the release switch configured to operatively connect to the pair of tensioned wires, the release switch further configured to at least partially release tension from the pair of tensioned wires, whereby releasing the tension enables the pair of tensioned wires in the head end of the at least one toothbrush to disengage from the pair of depressions of the at least one detachable head;

a docking platform, the docking platform comprising at least one toothbrush reception portion, the at least one toothbrush reception portion configured to receive the handle end of the toothbrush, the docking platform further comprising at least one head reception portion, the at least one head reception portion configured to receive the at least one disposable head; and an ultraviolet portion, the ultraviolet portion comprising a stand, a hood, and a light source, the stand disposed adjacent to the at least one toothbrush, the hood configured to selectively cover the at least one detachable head, the hood comprising an interior reflective surface, the light source configured to emit an ultraviolet light, whereby the ultraviolet light reflects off the interior reflective surface for substantially immersing the at least one detachable head with ultraviolet light.

2. The system of claim 1, wherein the at least one toothbrush is a manual toothbrush.

3. The system of claim 1, wherein the at least one toothbrush is three toothbrushes.

4. The system of claim 1, wherein the plurality of bristles in the at least one detachable head are fabricated from an antibacterial synthetic polymer.

5. The system of claim 1, wherein the at least one detachable head is six detachable heads.

6. The system of claim 1, wherein the back side of the at least one detachable head is textured.

7. The system of claim 1, wherein the cartridge is transparent.

8. The system of claim 1, wherein the pair of tensioned wires are parallel.

9. The system of claim 1, wherein the pair of tensioned wires terminate at a hook.

10. The system of claim 1, wherein the hook is configured to engage the pair of depressions.

11. The system of claim 1, wherein the release switch is disposed at the head end of the toothbrush.

12. The system of claim 1, wherein the release switch is configured to be operable with one hand.

13. The system of claim 1, wherein the at least one disposable head comprises a pair of lateral edges, the pair of lateral edges configured to slidably receive the pair of tensioned wires.

14. The system of claim 1, wherein the docking platform has a substantially rectangular shape.

15. The system of claim 1, wherein the docking platform is fabricated from an antibacterial polymer.

16. The system of claim 1, wherein the hood selectively covers the at least one detachable head during attachment to the head end of the at least one toothbrush, and during storage in the at least one head reception portion of the docking platform.

17. The system of claim 1, wherein the hood is configured to pivot.

18. The system of claim 1, wherein the hood is dome-shaped.

19. The system of claim 1, wherein the stand is configured to telescopically extend and retract.

20. The system of claim 1, wherein the light source is an excimer lamp.

* * * * *